(12) United States Patent
Samuelsson

(10) Patent No.: US 6,245,049 B1
(45) Date of Patent: Jun. 12, 2001

(54) DEVICE FOR STOMA HYGIENE

(76) Inventor: Karl-Erik Samuelsson, Granhacksvagen 29, S-445 55, Surte (SE)

(*) Notice: Subject to any disclaimer, the term of this patent is extended or adjusted under 35 U.S.C. 154(b) by 0 days.

(21) Appl. No.: 09/308,658
(22) PCT Filed: Dec. 2, 1997
(86) PCT No.: PCT/SE97/02015
§ 371 Date: Jul. 29, 1999
§ 102(e) Date: Jul. 29, 1999
(87) PCT Pub. No.: WO98/24387
PCT Pub. Date: Jun. 11, 1998

(30) Foreign Application Priority Data

Dec. 3, 1996 (SE) .................................. 9604440

(51) Int. Cl.[7] .................................................. A61M 31/00
(52) U.S. Cl. .................................................. 604/276
(58) Field of Search .................................. 604/276, 277, 604/327, 332–335, 337, 338, 339, 341, 342, 343, 355, 356

(56) References Cited

U.S. PATENT DOCUMENTS 2,776,660 * 1/1957 Fortin ........................................ 128/66
3,017,887 * 1/1962 Heyer ...................................... 128/348
3,042,041 * 7/1962 Jascalevich ............................ 128/276
3,957,082 * 5/1976 Fuson et al. ......................... 137/625.41

* cited by examiner

Primary Examiner—Sharon Kennedy
Assistant Examiner—Ann Y. Lam
(74) Attorney, Agent, or Firm—Dennison, Scheiner, Schultz & Wakeman

(57) ABSTRACT

A device for stoma hygiene includes a cover having a first end and a second end, the first end being generally open, and being constructed and arranged to seal against a stoma to be cleansed, and a ball joint disposed at the second end of the cover which is generally closed, the ball joint sealing against the cover and having a passage therethrough extending into the cover at a first end of the passage, and having a spray for liquid disposed at the second end of the passage, the spray being disposed within the cover and being generally directed towards the first end of the cover. A generally rigid tube is sealingly attached to the passage at the first end of the passage, the generally rigid tube enabling movement of the ball joint to aim the spray means, and a drain for liquid is disposed in the cover adjacent the first end of the cover, and passing through the cover. The generally rigid tube is attached to a source of water at an end thereof opposite to the passage.

6 Claims, 2 Drawing Sheets

DEVICE FOR STOMA HYGIENE

BACKGROUND OF THE INVENTION

The present invention relates to a device for cleansing the end of an intestine protruding from a human body, which is normally covered by a plastic pouch. The protruding part of the intestine must be regularly cleansed and this entails problems since the intestine itself is of organic material and has uneven surfaces. Hitherto soap, water and a compress have been used, but this is an elaborate procedure and requires much time.

SUMMARY OF THE INVENTION

The object of the present invention is to facilitate cleansing of the end of an intestine protruding from a human body. This is achieved by placing a cover over the part of the body where the intestine protrudes, the edge of the cover being such that it is always in close contact with the part of the body where the intestine protrudes. A joint is provided at the upper end of the cover, said joint being in the nature of a ball and being movable. The joint has a through-channel. The outlet end of the channel is located in the cover itself and is provided with a strainer, allowing liquid to flow through the channel and to be thoroughly spread inside the cover. The channel in the joint is connected to a unit for supplying the joint with liquid from a liquid source such as a conventional water tap, for instance, where hot and cold water can be mixed to a suitable temperature. Said part may be rigid and then functions as a guide means for the joint so that the entire surface covered by the cover can be rinsed.

BRIEF DESCRIPTION OF THE DRAWINGS

The present invention will be described in more detail with reference to the accompanying drawings in which.

DESCRIPTION OF THE PREFERRED EMBODIMENTS

Figure 1:
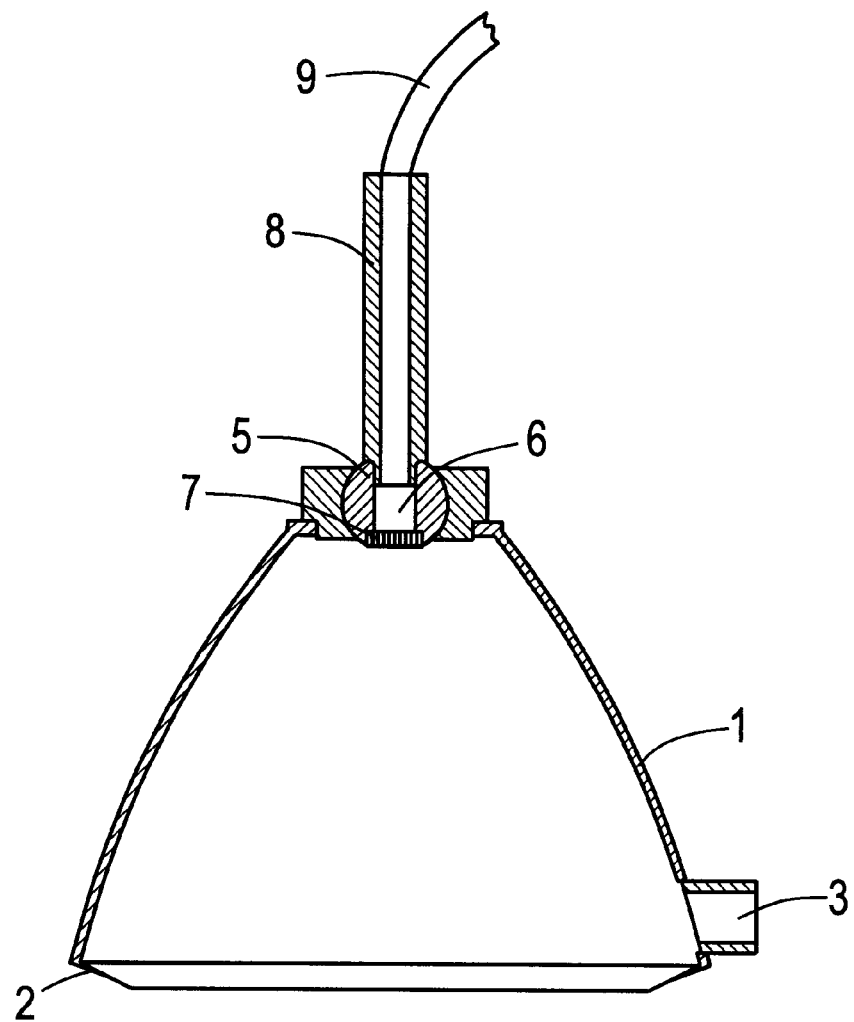
FIG. 1 shows an embodiment of a cover according to the present invention by way of example.
Figure 2:
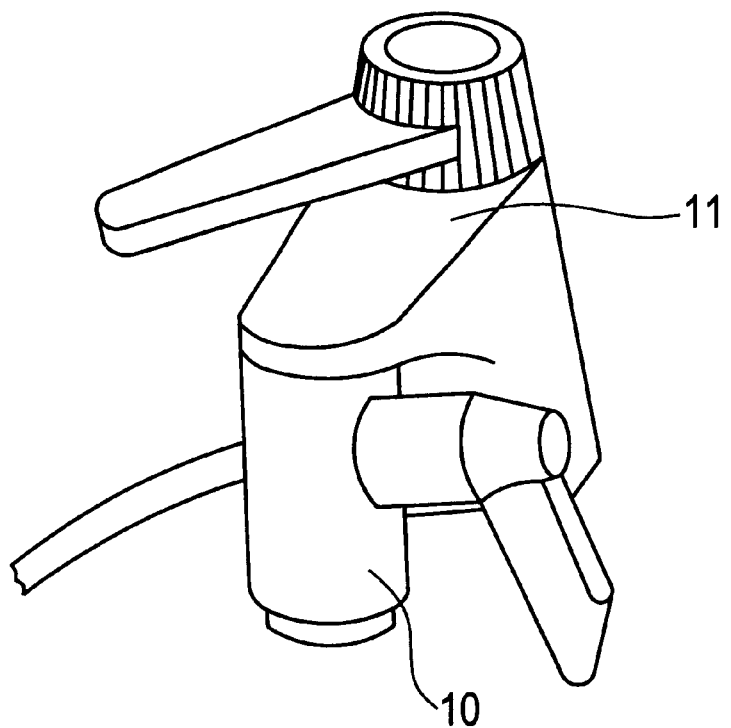
FIG. 2 shows its connection to a conventional water tap.

The drawings show a cover 1 having a peripheral edge 2 that may be elastic so that when the cover is placed over a stoma, its peripheral edge will fit tightly against the surface of the body. The cover 1 may suitably consist of transparent material so that cleansing can be supervised. The cover 1 is provided at the bottom with an outlet 3 that may be connected to a hose leading to a toilet bowl or other drain. At the top the cover is provided with a ball 5 that is movably journalled. The ball has a through-channel 6, and a strainer 7 is provided at the inner end to spread the liquid passing through the channel. A tube 8 is connected to the inlet opening of the channel, said tube being in turn connected to a hose 9. A stopcock 10 is provided at the other end of the hose 9 and can easily be attached to an ordinary water tap 11 in a water supply system. The tube 8 acts as guide means for the ball, allowing liquid to be sprayed over the entire surface covered by the cover. When the stopcock 10 has been attached to an ordinary water tap 11 in a water supply system and the tap turned on, liquid runs straight through the stopcock 10 so that the temperature of the liquid can be adjusted. The stopcock 10 is then turned so that the liquid flows to the shower in the cover 1. The stopcock 10 is adjustable for a certain maximum flow pressure and can be regulated steplessly from a small pressure to the maximum flow pressure. A shut-off device (not shown in the drawings) is provided on the tube 8 in the form of a non-return valve that can be operated manually.

What is claimed is:

1. A device for stoma hygiene, comprising:

a cover having a first end and a second end, the first end being generally open, and being constructed and arranged to seal against a stoma to be cleansed;

a ball joint disposed at the second end of the cover which is generally closed, the ball joint sealing against the cover and comprising a passage therethrough extending into the cover at a first end of the passage, and having a spray means for liquid disposed at the second end of the passage, the spray means being disposed within the cover and being generally directed towards the first end of the cover;

a generally rigid tube sealingly attached to the passage at the first end of the passage, the generally rigid tube comprising means for moving the ball joint to aim the spray means;

drainage means for liquid disposed in the cover adjacent the first end of the cover, and passing through the cover; and means for attaching the generally rigid tube to a source of water at an end thereof opposite to the passage.

2. A device according to claim 1, wherein the means for attaching comprises a shut-off means which can be operated with one hand.

3. A device according to claim 2, wherein the shut-off means comprises a stopcock having a first position which directs a flow of water to the cover, and a second position which directs the flow of water to a drain.

4. A device according to claim 3, wherein the stopcock comprises means for attachment to a water faucet.

5. A device according to claim 3, wherein the stopcock comprises means for regulating pressure of a flow of water directed to the cover.

6. A device according to claim 1, wherein the cover comprises elastic means for sealing against the stoma.

* * * * *